(12) United States Patent
Kluger et al.

(10) Patent No.: US 11,331,499 B2
(45) Date of Patent: May 17, 2022

(54) MEDICAL DEVICE IMPLANT CARRIER FOR FRAGILE MEDICAL IMPLANTS

(71) Applicant: University of Utah Research Foundation, Salt Lake City, UT (US)

(72) Inventors: David Kluger, Salt Lake City, UT (US); Gregory Clark, Salt Lake City, UT (US); Douglas Hutchinson, Salt Lake City, UT (US); David Page, Salt Lake City, UT (US); Suzanne Wendelken, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 132 days.

(21) Appl. No.: 16/321,384

(22) PCT Filed: Jul. 28, 2017

(86) PCT No.: PCT/US2017/044427
§ 371 (c)(1),
(2) Date: Jan. 28, 2019

(87) PCT Pub. No.: WO2018/023026
PCT Pub. Date: Feb. 1, 2018

(65) Prior Publication Data
US 2019/0160289 A1 May 30, 2019

Related U.S. Application Data

(60) Provisional application No. 62/367,953, filed on Jul. 28, 2016.

(51) Int. Cl.
*A61N 1/372* (2006.01)
*A61N 1/36* (2006.01)

(52) U.S. Cl.
CPC ..... *A61N 1/37205* (2013.01); *A61N 1/36128* (2013.01); *A61N 1/36057* (2013.01); *A61N 1/36071* (2013.01)

(58) Field of Classification Search
CPC ............ A61N 1/37205; A61N 1/36128; A61N 1/36057; A61N 1/36071
See application file for complete search history.

(56) References Cited

U.S. PATENT DOCUMENTS 4,763,788 A 8/1988 Jorneus et al.
5,443,492 A 8/1995 Stokes et al.
(Continued)

FOREIGN PATENT DOCUMENTS

CN 104688283 6/2015
FR 2932979 A1 1/2010

OTHER PUBLICATIONS

PCT Application No. PCT/US17/44427 Filing Date Jul. 28, 2017, David Kluger, International Search Report, dated Dec. 11, 2017; 12 Pages.

*Primary Examiner* — Christopher A Flory
(74) *Attorney, Agent, or Firm* — Thorpe North and Western LLP (57) ABSTRACT

A medical implant device (100) is disclosed that can protect and shield an implant (101) as the implant (101) moves through body tissue. The medical implant device (100) can comprise a main body portion (110) having a payload opening (111) to receive a payload (i.e., an implant). The medical implant device (100) can also comprise a tapered nose portion (120) at a front end (103*a*) of the medical implant device (100) extending from the main body portion (110) and configured to penetrate body tissue. In addition, the medical implant device (100) can comprise a payload (Continued)

coupling interface (130) configured to couple the implant (101) to the main body portion (110).

27 Claims, 8 Drawing Sheets

(56) References Cited

U.S. PATENT DOCUMENTS

| | | | |
|---|---|---|---|
| 6,436,068 B1* | 8/2002 | Bardy | A61M 37/0069 604/57 |
| 6,565,594 B1 | 5/2003 | Herweck et al. | |
| 6,863,692 B2 | 3/2005 | Meulink | |
| 6,916,335 B2 | 7/2005 | Kanji | |
| 7,819,880 B2 | 10/2010 | Zannis et al. | |
| 7,942,924 B1* | 5/2011 | Perez | A61F 2/966 623/1.23 |
| 8,262,687 B2 | 9/2012 | Igaki | |
| 8,308,789 B2 | 11/2012 | Armstrong | |
| 9,364,361 B2 | 6/2016 | Duong et al. | |
| 9,387,105 B2 | 7/2016 | Andress et al. | |
| 10,518,095 B2* | 12/2019 | Ho | A61N 1/3756 |
| 2004/0054388 A1 | 3/2004 | Osypka | |
| 2004/0098134 A1* | 5/2004 | Meulink | A61F 2/3609 623/23.52 |
| 2005/0033319 A1* | 2/2005 | Gambale | A61B 17/0469 606/139 |
| 2006/0122676 A1* | 6/2006 | Ko | A61M 25/0668 607/116 |
| 2007/0299300 A1* | 12/2007 | Smith | A61B 17/06109 600/30 |
| 2009/0099415 A1* | 4/2009 | Imran | A61F 5/0003 600/106 |
| 2009/0193996 A1* | 8/2009 | Brydges-Price | F42B 12/54 102/502 |
| 2010/0030227 A1* | 2/2010 | Kast | A61B 17/3468 606/129 |
| 2010/0305656 A1* | 12/2010 | Imran | A61N 1/0517 607/40 |
| 2011/0190786 A1 | 8/2011 | Gerber et al. | |
| 2011/0218488 A1* | 9/2011 | Boyko | A61M 31/00 604/57 |
| 2013/0267837 A1 | 10/2013 | Schulte et al. | |
| 2014/0018818 A1* | 1/2014 | Somogyi | A61N 1/372 606/129 |
| 2014/0135895 A1* | 5/2014 | Andress | A61F 2/97 623/1.12 |
| 2014/0144000 A1* | 5/2014 | Creaven | A61F 2/9525 29/505 |
| 2014/0163579 A1* | 6/2014 | Tischendorf | A61N 1/3756 606/129 |
| 2014/0163580 A1* | 6/2014 | Tischendorf | A61N 1/0551 606/129 |
| 2014/0200592 A1* | 7/2014 | O'Connor | A61N 1/0587 606/129 |
| 2014/0213979 A1* | 7/2014 | Boyko | A61M 31/002 604/164.09 |
| 2014/0276928 A1* | 9/2014 | Vanderpool | A61B 17/3468 606/129 |
| 2014/0309722 A1 | 10/2014 | Igaki et al. | |
| 2015/0257910 A1* | 9/2015 | Duong | A61F 2/97 623/1.11 |
| 2015/0273212 A1* | 10/2015 | Berthiaume | A61M 25/0108 600/424 |
| 2015/0306378 A1* | 10/2015 | Schmidt | A61B 6/12 600/424 |
| 2016/0015499 A1* | 1/2016 | Scott | F42B 10/34 604/130 |
| 2016/0038741 A1* | 2/2016 | Perryman | A61N 1/36071 607/46 |
| 2016/0074167 A1 | 3/2016 | Vautrin | |
| 2016/0114163 A1* | 4/2016 | Franke | A61N 1/36046 607/53 |
| 2018/0168564 A1* | 6/2018 | Tischendorf | A61N 1/0551 |
| 2018/0296338 A1* | 10/2018 | Rabito | A61F 2/2436 |

* cited by examiner

MEDICAL DEVICE IMPLANT CARRIER FOR FRAGILE MEDICAL IMPLANTS

RELATED APPLICATION(S)

This application claims priority to U.S. Provisional Application No. 62/367,953, filed Jul. 28, 2016, which is incorporated herein by reference.

GOVERNMENT INTEREST

None.

BACKGROUND

Medical technology currently provides the ability to implant small medical devices in a patient's body for a range of medical applications. One type of implant can interface with the nervous system for a variety of purposes, such as enabling muscle control, enabling control of a prosthetic, and/or providing a sense of touch. One such neural interface, the Utah slanted electrode array (USEA), may include 100 or more electrodes configured to penetrate a nerve to provide electrical communication with the nerve. The neural interface implant is typically attached to an electrical wire and coupled to the nerve at an interface site inside the patient's body. The wire runs from the implant to a "control box" outside the patient's body, which can be in communication with the patient's brain or other signal input source.

SUMMARY

Although a wide variety of locations are contemplated and can be used, a typical neural interface implant site may be located in an interior of a patient's upper arm, next to the biceps above the elbow. With a wire extending from the implant site, this location may be inconvenient for the patient's movement and comfort in dealing with the wire. In response to this, the wire may be configured to exit the patient's body at a different, more convenient location, such as toward the outside of the back of the upper arm near the triceps. Because the neural interface site remains the same, the implant is moved through the patient's body from the wire exit location at the upper back of the arm by the triceps toward the neural interface site near the biceps, thus, effectively "running" wire through the patient's body. This can be problematic, however, considering the many sharp electrodes exposed on the implant that grab and catch on the body tissue (e.g., muscle, fat, connective tissue, etc.) as the implant is moved through the body. Such body tissue can severely damage fragile electrodes and reduce the implant's ability to properly interface with the nerve, thus destroying the purpose of the implant.

Accordingly, a medical implant device is disclosed that can protect and shield an implant as the implant moves through body tissue to an implant site. The medical implant device can comprise a main body portion having a payload opening to receive a payload (i.e., an implant). The medical implant device can also comprise a tapered nose portion at a front end of the medical implant device extending from the main body portion and configured to penetrate body tissue. In addition, the medical implant device can comprise a payload coupling interface configured to couple the payload to the main body portion.

A method for implanting a medical device is also disclosed. The method can comprise forming a first opening in a body of a patient. The method can also comprise forming a second opening in the body of the patient. The method can further comprise disposing a medical implant device in the first opening in the body, the medical implant device containing a medical device. The method can still further comprise inserting a surgical instrument in the second opening in the body. Additionally, the method can comprise pulling the medical implant device toward the second opening in the body with the surgical instrument.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

These drawings are provided to illustrate various aspects of the invention and are not intended to be limiting of the scope in terms of dimensions, materials, configurations, arrangements or proportions unless otherwise limited by the claims.

DETAILED DESCRIPTION

Although these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a suture" includes reference to one or more of such materials and reference to "inserting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 5%, and most often less than 1%, and in some cases less than 0.01%.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Implant Carrier and Methods of Use

Figure 1:
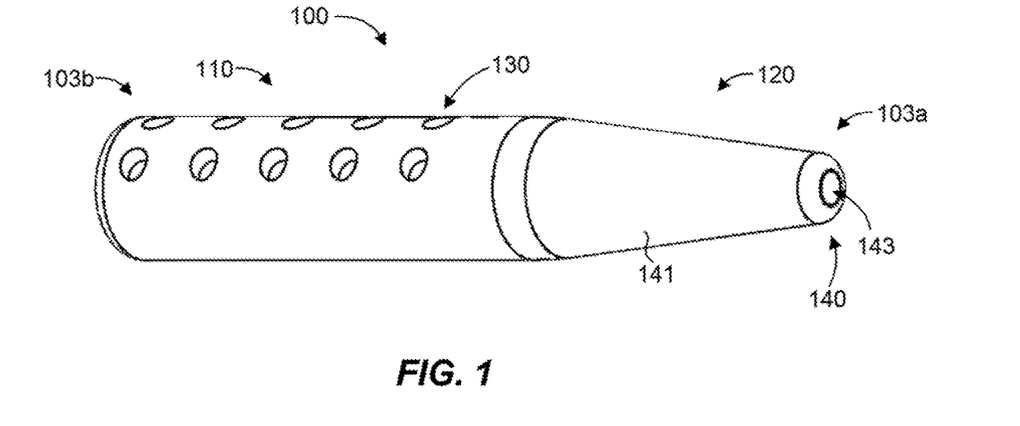
FIG. 1 illustrates a medical implant device in accordance with an example of the present disclosure.
Figure 2:
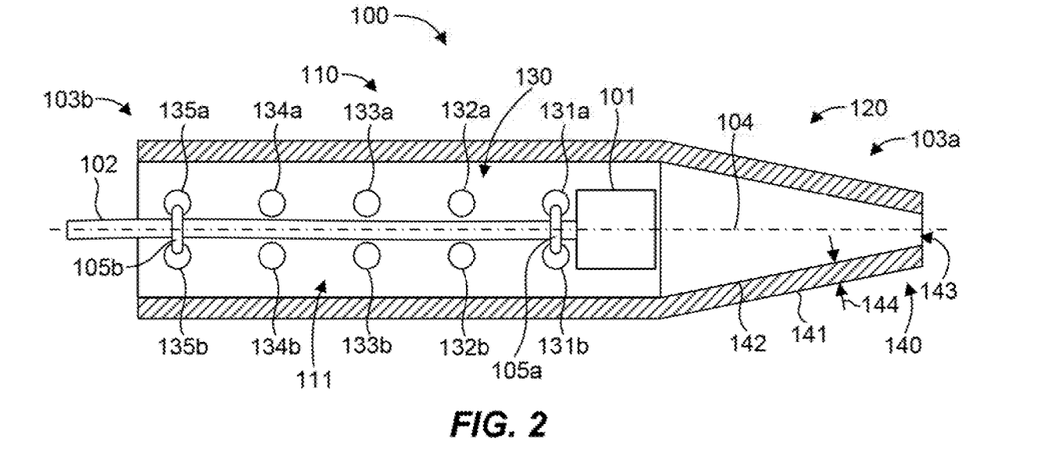
FIG. 2 is a cross-section of the medical implant device of FIG. 1, shown coupled to an implant in accordance with an example of the present disclosure.

FIG. 1 illustrates a medical implant device or carrier 100 in accordance with an example of the present disclosure. A cross-sectional representation of the carrier 100 is shown in FIG. 2 with a payload or implant 101 that can be carried by the carrier 100. In some embodiments, the implant 101 can be coupled to a wire 102, such as to facilitate communication (e.g., data, power, etc.) between the implant 101 and an external device, such as a control box that may include a processor, a memory device, a power source, etc.

The carrier 100 can include a main body portion 110 and a tapered nose portion 120, which can be configured to penetrate body tissue, such as fatty tissue, muscle, etc. The tapered nose portion 120 can be located at a front end 103a of the carrier 100 and can extend from the main body portion 110 (e.g., with no substantial gap or separation between the tapered nose portion 120 and the main body portion 110). In one aspect, the main body portion 110 and the tapered nose portion 120 can be integrally formed with one another in a monolithic structure, although other configurations are possible, such as a multipiece construction.

The main body portion 110 can have a payload opening 111 to receive the implant 101 within the carrier 100 to facilitate shielding and protecting the implant 101 as the carrier 100 moves through body tissue. The payload opening 111 can be exposed at a back end 103b of the carrier 100 opposite the front end 103a. In one aspect, the payload opening 111 can be configured to receive the implant 101 via the back end 103b of the carrier 100. In this case, the wire 102 can extend from the implant 101 and out the back end 103b of the carrier 100 via the payload opening 111. Although the implant 101 is shown contained or disposed entirely within the main body portion 110 of the carrier 100, it should be recognized that some or all of the implant 101 can be contained or disposed in the nose portion 120 of the carrier 100, in which case the nose portion 120 includes a payload opening. The main body portion 110 can have any suitable configuration, such as a cylindrical configuration as shown, which can form a hollow tube or other such vessel for housing the implant 101, although other cross-sectional shapes can be used such as, but not limited to, elliptical, rounded square, tear drop, etc. The payload opening 111 can be of any suitable shape, size, etc. to accommodate a given implant.

For example, the payload opening can be sized to accommodate a payload having maximum width and height dimensions (e.g. transverse and longitudinal axis of the carrier 100) from about 1 mm to about 20 mm, and often from 4 to 8 mm, and in some cases about 5 mm. As a general guideline, the carrier dimensions can also vary. However, typically the carrier can have a length from about 1 cm to about 8 cm, and most often from 3 to 5 cm. The carrier can also have wall thicknesses ranging from about 0.4 mm to about 4 mm, and often from 0.5 to 1.5 mm, depending on the material and design used to construct the carrier.

Figure 3:
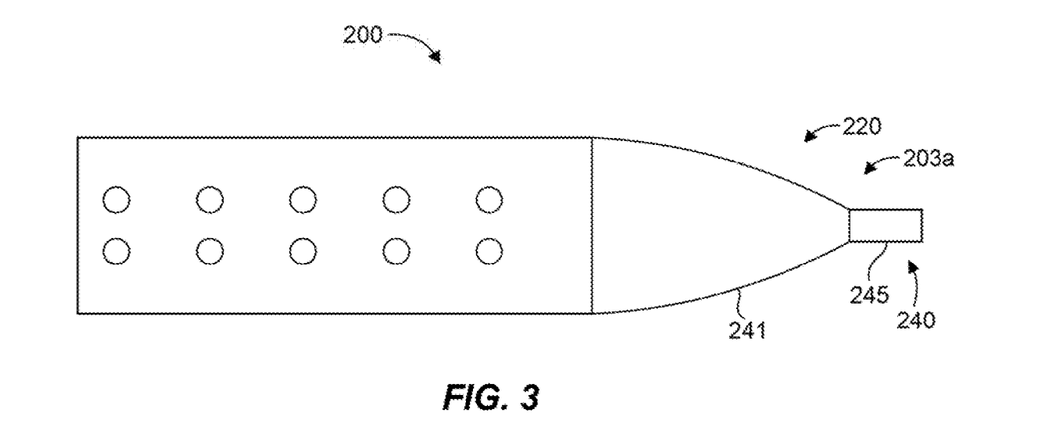
FIG. 3 illustrates a medical implant device in accordance with another example of the present disclosure.

As mentioned above, the tapered nose portion 120 can be configured to penetrate body tissue. The tapered nose portion 120 can have any suitable shape or configuration that may facilitate penetration of body tissue, such as a conical shaped outer surface (e.g., a straight or linear taper) as shown in FIGS. 1 and 2. In some embodiments, as shown in FIG. 3, a tapered nose portion 220 can comprise a bullet shaped outer surface 221 (e.g., a rounded or non-linear convex taper) to penetrate body tissue and minimize drag through body tissue.

The carrier 100 can also include a payload coupling interface 130 configured to couple the implant 101 to the carrier 100, such as to the main body portion 110. In one embodiment, the payload coupling interface 130 can comprise one or more securing holes 131a-b, 132a-b, 133a-b, 134a-b, 135a-b in the main body portion 110 to facilitate securing the implant 101 to the main body portion 110, such as by tying with a thread (e.g., a surgical suture). In some embodiments, securing holes can be configured as a pair of securing holes, with each of the securing holes in the pair located at the same longitudinal position of the main body portion 110. For example, the securing holes 131a-b can be arranged in a pair, the securing holes 132a-b can be arranged in a pair, the securing holes 133a-b can be arranged in a pair, the securing holes 134a-b can be arranged in a pair, and the securing holes 135a-b can be arranged in a pair. Each pair of securing holes 131a-b, 132a-b, 133a-b, 134a-b, 135a-b can be located at a different longitudinal position of the main body portion 110 along a longitudinal axis 104 of the carrier 100. This can provide multiple securing location options for securing the implant 101, and optionally the wire 102, to the carrier 100. In one aspect, the pairs of securing holes 131a-b, 132a-b, 133a-b, 134a-b, 135a-b can all be located on the same side of the main body portion. In one optional aspect, the pairs of securing holes can be oriented within an angle of 90° and most often within 45° of one another, along an arc of the carrier surface as measured radially from a central longitudinal axis of the carrier. In another aspect, two or more of the securing holes can be oriented parallel to one another through the main body portion 110, such as each securing hole in a pair, although the securing holes can be oriented at any suitable angle relative to one another. Typically, the pairs of securing holes can be oriented sufficiently close to one another that the wire is frictionally engaged against an interior surface of the carrier when corresponding sutures are in place through the securing holes.

In the illustrated example, the pair of securing holes 131a-b can be utilized to secure the wire 102 near the implant 101 with a thread or suture 105a, and the pair of securing holes 135a-b can be utilized to secure the wire 102 farther away from the implant 101 (e.g., near the back end 103b of the carrier 100) with a thread or suture 105b. It should be recognized that the securing holes can be utilized in any combination, as desired, to couple or secure the implant 101 to the carrier 100, such as with threads or sutures. A surgical suture, which is typically a stitch used by doctors and surgeons to hold tissue together, can be utilized in accordance with the present disclosure to secure or couple the implant 101 and associated wire 102 (as applicable) to the carrier 100. Application of a surgical suture generally involves using a needle with an attached length of suture thread that is looped through two or more of the securing holes and around the wire 102 (or a portion of the implant 101, depending on the implant), and tied in a knot (e.g., a surgical knot). Suture thread of any suitable shape, size, or material (e.g., hypoallergenic absorbable or non-absorbable materials such as nylon, polyester, PVDF, polypropylene, etc.) may be utilized.

In some embodiments, the carrier 100 can include a manipulation interface 140 at the front end 103a of the carrier 100 to facilitate grasping the carrier 100 with a surgical instrument (e.g., a hemostat, forceps, etc.) and pulling the carrier 100 through the body tissue. In one aspect, the manipulation interface 140 can comprise an outer surface 141 and an inner surface 142 of the tapered nose portion 120. The inner surface 142 can be defined at least partially by a front opening or hole 143 in the tapered nose portion 120 exposed at the front end 103a of the carrier 100. The outer and inner surfaces 141, 142 of the tapered nose portion 120 can be oriented at any suitable angle relative to one another to facilitate grasping the carrier 10 with a surgical instrument and pulling the carrier 100 through the body tissue, such as from about 10 degrees (e.g., a greater wall thickness 144 toward the back end 103b of the carrier 100) to about −10 degrees (e.g., a greater wall thickness 144 toward the front end 103a of the carrier 100), and often ±0.1 to ±10 degrees. In some embodiments, the outer and inner surfaces 141, 142 of the tapered nose portion 120 can be parallel (e.g., a constant wall thickness 144).

The carrier 100 can have any suitable shape or configuration that may facilitate grasping the carrier 100 with a surgical instrument and pulling the carrier 100 through the body tissue, such as the front opening 143 and inner and outer surfaces 141, 142 of the tapered nose portion 120, as shown in FIGS. 1 and 2. In some embodiments, as shown in FIG. 3, a carrier 200 can have a manipulation interface 240 that comprises a tab or protrusion 245 extending from a front end 203a of a tapered nose portion 220. The tab or protrusion 245 can have any suitable configuration, such as a flat configuration (e.g., at least two parallel flat surfaces), a cylindrical configuration, a spherical bulb configuration, hole allowing a hook or suture to pass therethrough to facilitate grasping, etc. The tab or protrusion 245 can be located at the front end 203a of the carrier 200 and configured to provide a grasping interface for pulling the carrier 200 through body tissue while also minimizing the drag on the body tissue resulting from the tab or protrusion 245.

A carrier and its components as disclosed herein can be made of any suitable material, such as polymers (e.g., hard rubber, plastics, etc.), ceramics, metals, etc. For example, materials will typically be biocompatible such that the material does not cause a biological response when introduced to internal tissue. Suitable materials may meet ISO 10933 and/or USP Class VI biocompatibility standards. In one aspect, suitable materials can withstand a sterilization procedure used on the implant device, which may be associated with the carrier at the time of sterilization. In the case of USEAs, this means the material must be able to withstand ethylene oxide (EtO) sterilization. In another aspect, suitable materials may be thermally stable enough to withstand high pressure and heat in an autoclave, to which an implant and associated carrier may be subjected for sterilization. Non-limiting examples of suitable material can include polymers such as polypropylene, polycarbonate, polyetheretherketone, high or ultra-high density polyethylene, nylon, polyvinylchloride, polysulfone, polyethersulfone polyetherimide, polytetrafluoroethylene, or copolymers of any of these plastics; ceramics such as silicon carbide, titanium nitrides, aluminum oxide, zirconium dioxide, graphite; carbon fiber composites, and metal such as titanium, medical-grade stainless steel, gold, platinum, cobalt, or chromium; and alloys and composites thereof.

Suitable materials may also exhibit adequate stiffness, as quantified by its flexural modulus. Typically, a flexural modulus of greater than 0.5 GPa may be adequate, with greater than 1.5 GPa being particularly useful. Suitable materials may also have a hardness greater than Shore A 65. A suitable material for the carrier will also be strong enough to withstand the stresses of being pulled through tissue. This can be quantified by its elastic (Young's) modulus and tensile strength, which defines the relationship between stress (force per unit area) and strain (proportional deformation) in a material, and the tensile stress at which it fails, respectively. A suitable material can often have a Young's modulus greater than 0.5 GPa, with a tensile strength greater than 15 MPa.

A suitable material may be capable of having a surface finish that enables it to be pulled easily through tissue, meaning its coefficient of friction with the tissue is sufficiently low (e.g., less than 0.5). In a practical sense, the coefficient of friction between the carrier and the muscle should be low enough so a typical surgeon can use his own strength (i.e., without using excess force) to pull the carrier through tissue without causing the tissue to rip, tear, shred, or slice excessively. A suitable material will also not absorb copious amounts of water (e.g., less than 5% water absorption by volume). If too much water is absorbed, the carrier could swell and inhibit safe removal of the implant.

In addition, the carrier, not just the raw material from which it is made, should not be brittle. Brittleness can be caused by at last three factors: intrinsic material properties, physical dimensions, and the methods used to make the carrier. A suitable material will be able to undergo some plastic deformation before failure. A brittle material will not undergo plastic deformation when stretched and will violently snap when it reaches a certain amount of stress. A carrier made from a non-brittle material can snap before plastic deformation occurs. For example, a 3D-printed polycarbonate carrier can be brittle and might break under low tension even though polycarbonate is a very strong, non-brittle material.

It should be recognized that certain components of a carrier may vary from the above material guidelines in some respects, such as an interior component that does not contact tissue or a component that is not subjected to the stresses involved in pulling the carrier through tissue. In some cases, a part or component may require higher strength materials as dictated by the particular design of the component and carrier.

FIGS. 4A-4D illustrate aspects of a medical implant device or carrier 300 in accordance with another example of the present disclosure. The carrier 300 is similar in many respects to the carriers 100 and 200 described above. For example, the carrier 300 can include a main body portion 310 and a tapered nose portion 320. The carrier 300 can also include a payload coupling interface 330 that comprises one or more securing holes in the main body portion 310. The carrier 300 can additionally include a manipulation interface 340 at a front end 303a of the carrier 300 defined at least partially by a hole in the tapered nose portion 320 that is exposed at the front end 303a of the carrier 300.

In this case, the main body portion 310 includes a payload receptacle 312 (FIG. 4B) and a payload cover 313 (FIG. 4C) that at least partially define a payload opening 311 (FIG. 4D) for an implant (not shown). The securing holes of the payload coupling interface 330 are associated with the payload receptacle 312, although it should be recognized that such securing holes can be associated with the payload cover 313 and/or the payload receptacle 312. The payload cover 313 can be movable relative to the payload receptacle 312 to facilitate disposing an implant in the payload opening 311. For example, the payload receptacle 312 can have longitudinally oriented openings 314a, 314b. The longitudinally oriented opening 314a can be formed in one or more bosses 316a, 316a' on the payload receptacle 312 configured to be on a lateral side of the carrier 300. The longitudinally oriented opening 314b can be formed in one or more bosses 316b, 316b' on the payload receptacle 312 configured to be on another (e.g., opposite) lateral side of the carrier 300. The payload cover 313 can have longitudinally oriented openings 315a, 315b. The longitudinally oriented opening 315a can be formed in one or more bosses 317a on the payload cover 313 configured to be on a lateral side of the carrier 300. The longitudinally oriented opening 315b can be formed in one or more bosses 317b on the payload cover 313 configured to be on another (e.g., opposite) lateral side of the carrier 300.

Figure 4A:
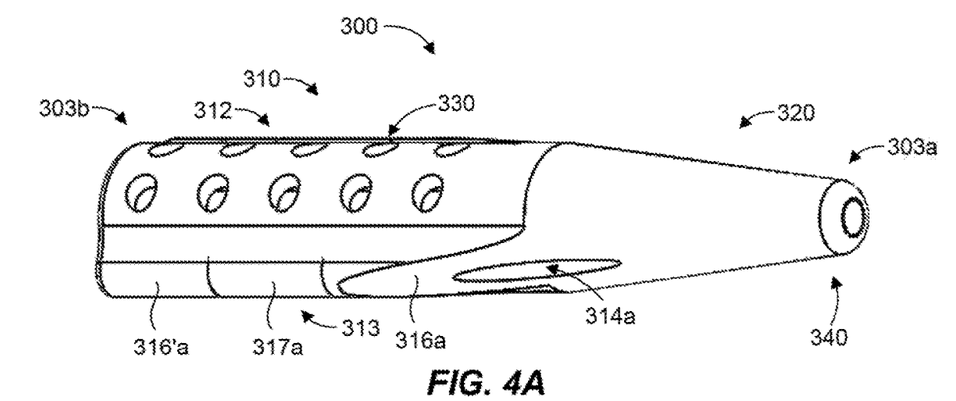
FIGS. 4A-4D illustrate aspects of a medical implant device in accordance with another example of the present disclosure.
Figures 4B, 4C:
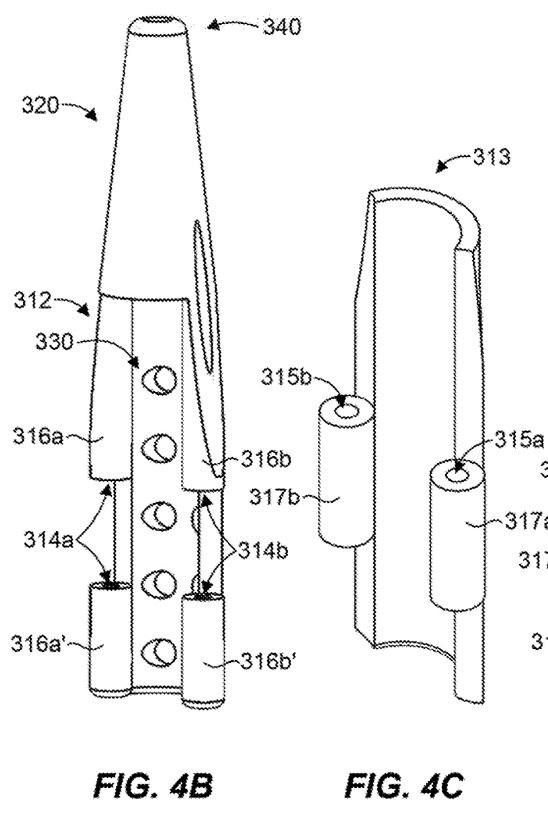

The longitudinally oriented opening 314a of the payload receptacle 312 and the longitudinally oriented opening 315a of the payload cover 313 can be configured to be aligned with one another, such as by positioning the boss 317a of the payload cover 313 between the bosses 316a, 316a' of the payload receptacle 312. In addition, the longitudinally oriented opening 314b of the payload receptacle 312 and the longitudinally oriented opening 315b of the payload cover 313 can be configured to be aligned with one another, such as by positioning the boss 317b of the payload cover 313 between the bosses 316b, 316b' of the payload receptacle 312.

Figure 4D:
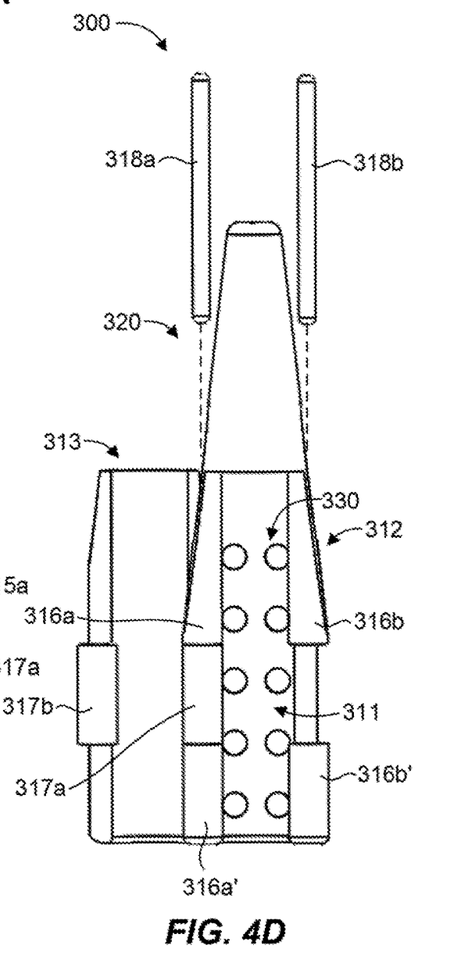

A removable coupling member (e.g., a pin) can be configured to be disposed in the longitudinally oriented openings to secure the payload cover 313 and the payload receptacle 312 to one another. For example, as shown in FIG. 4D, a pin 318a can be disposed in the longitudinally oriented openings 314a, 315a on a lateral side of the carrier 300, and a pin 318b can be disposed in the longitudinally oriented openings 314b, 315b on another (e.g., opposite) lateral side of the carrier 300 to secure the payload cover 313 and the payload receptacle 312 to one another.

In one aspect, the longitudinally oriented openings can be blind or terminated toward the back end 313b of the carrier 300, and can be open or exposed toward the front end 303a of the carrier 300. For example, the longitudinally oriented openings 314a, 314b can be open and exposed at the front end 303a of the carrier 300 and can terminate toward the back end 303b of the carrier 300. Thus, the pins 318a, 318b can be assembled from the front end 303a of the carrier 300 and can therefore be exposed toward the front end 303a of the carrier 300. The blind or terminated longitudinally oriented openings can capture the pins 318a, 318b in the openings and prevent movement of the pins out the back end 303b of the carrier 300 as the carrier moves through body tissue, which can prevent the pins from becoming dislodged and lost in the body tissue during use.

The removable coupling members (e.g., the pins 318a, 318b) can facilitate relative rotation (e.g., pivotal or hinge movement) of the payload receptacle 312 and the payload cover 313. In addition, the removable coupling members (e.g., the pins 318a, 318b) can facilitate removably coupling the payload receptacle 312 and the payload cover 313 with one another. Although two pins are shown in the illustrated example, which enables the payload receptacle 312 and the payload cover 313 to be distinct components that may be separated from one another, it should be recognized that the payload receptacle 312 and the payload cover 313 can be integrally formed with one another (e.g., via a compliant hinge). In this case, the payload receptacle 312 and the payload cover 313 can be secured to one another with only a single pin, which can prevent relative rotation of the payload receptacle 312 and the payload cover 313.

Figure 5A:
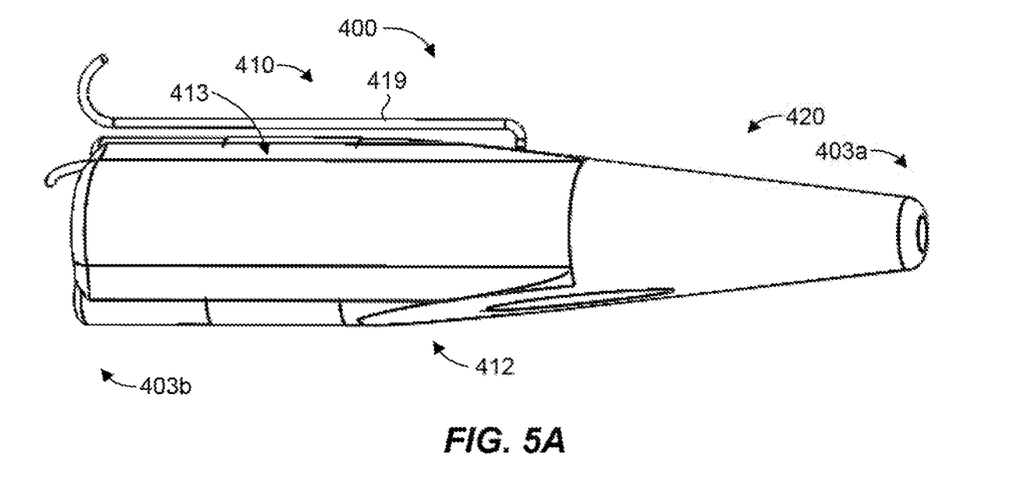
FIGS. 5A-5E illustrate aspects of a medical implant device in accordance with another example of the present disclosure.
Figure 5B:
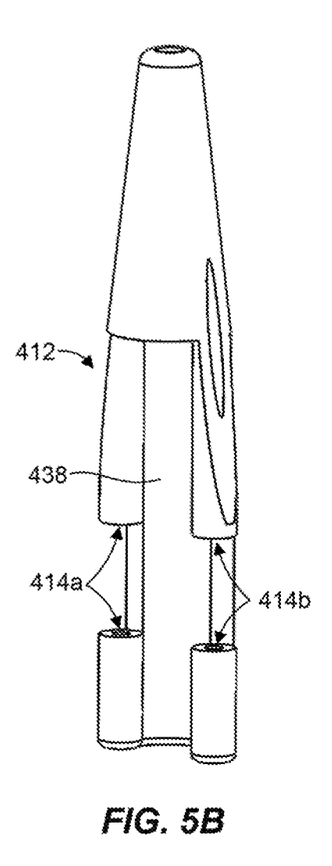
Figure 5C:
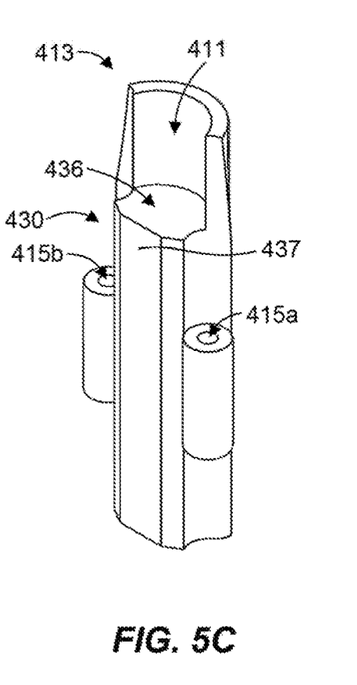
Figure 5D:
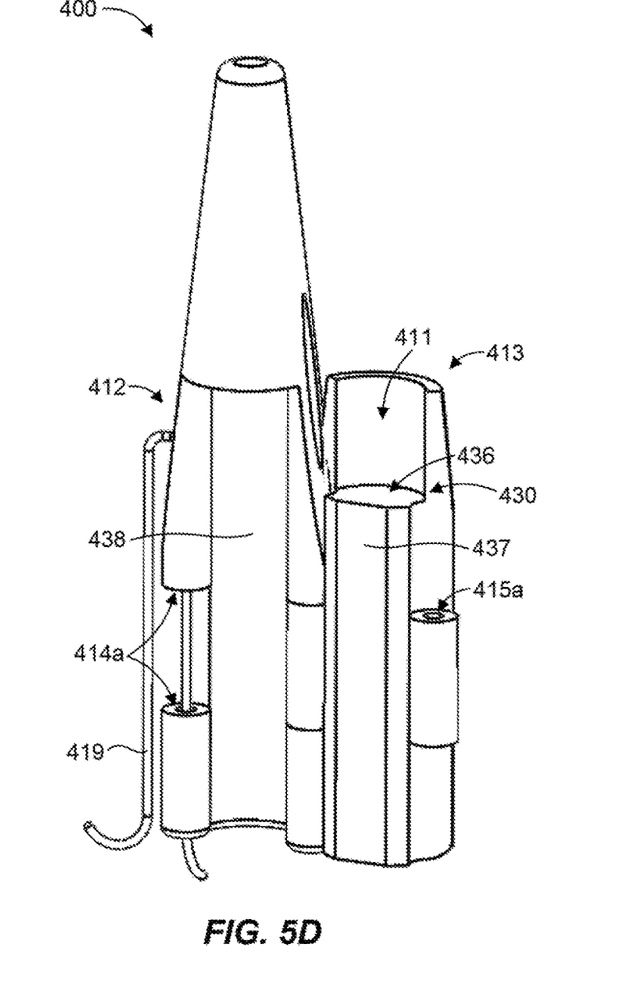
Figure 5E:
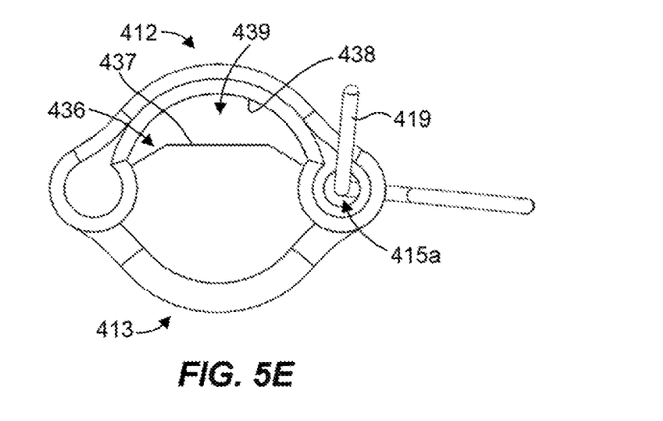

FIGS. 5A-5E illustrate aspects of a medical implant device or carrier 400 in accordance with another example of the present disclosure. The carrier 400 demonstrates variations on aspects described above with regard to the carrier 300. In this case, the carrier 400 includes a payload coupling interface 430 that comprises a protrusion or "bulge" 436 (see, e.g., FIGS. 5C-5E) extending from a payload cover 413 that defines a payload opening 411. Relative to the payload opening 411, the protrusion 436 is toward a back end 404b of the carrier 400 such that movement of an implant toward the back end 404b of the carrier 400 is prevented. In one aspect, the protrusion 436 can be configured to accommodate a wire from an implant (not shown) extending out the back end 404b of the carrier 400. For example, as shown in FIG. 5E, an outer surface 437 of the protrusion 436 can be configured to cooperate with an inner surface 438 of the payload receptacle 412 to form a channel, gap, space, or other such wire opening 439 configured to accommodate a wire from an implant extending out the back end 404b of the carrier 400. In some embodiments, the wire opening 439 can be configured such that the outer surface 437 of the protrusion 436 and the inner surface 438 of the payload receptacle 412 lightly compress the wire from the implant to further secure the implant in the carrier 400. The protrusion or bulge 436 can have any suitable configuration. For example, the protrusion 436 illustrated in the figures is solid and extends rearward the entire distance to the back end 413b of the carrier 400. In other embodiments, the protrusion 436 can be hollow, segmented, etc. to form the payload opening 411 and/or the wire opening 439 with any suitable surface or geometry to contact an implant and/or a wire in any suitable manner. Although the protrusion 436 is shown in the figures associated with the payload cover 413, it should be recognized that the protrusion 436 can be associated with the payload receptacle 412 and/or the payload cover 413.

In addition, one or more longitudinally oriented openings of the carrier 400 that receive removable coupling members can be configured as through holes that are open at the back end 403b of the carrier 400. For example, a longitudinally oriented opening 414a in the payload receptacle 412 can be configured as a through hole that is open at the back end 403b of the carrier 400. In the illustrated embodiment, a longitudinally oriented opening 414b can be configured as a blind hole that is closed or terminated at the back end 403b of the carrier 400. This can facilitate use of a removable coupling member in the form of a pin, as described above, which can provide a hinge connection between the payload receptacle 412 and the payload cover 413. The through hole configuration of the longitudinally oriented opening 414a can facilitate utilizing a removable coupling member in the form of a thread 419 that extends through the longitudinally oriented opening 414a in the payload receptacle 412 and through a longitudinally oriented opening 415a in the payload cover 413. The thread 419 can be tied in a knot (e.g., forming a suture) to secure the payload receptacle 412 and the payload cover 413 to one another. An implant can be removed from the carrier 400 by simply cutting the suture. Although the longitudinally oriented openings of the carrier 400 are configured to receive a suture and pin, it should be recognized that the longitudinally oriented openings of the carrier 400 can be configured to receive multiple sutures (e.g., secured by sutures on opposite lateral sides of the carrier 400).

Figure 6A:
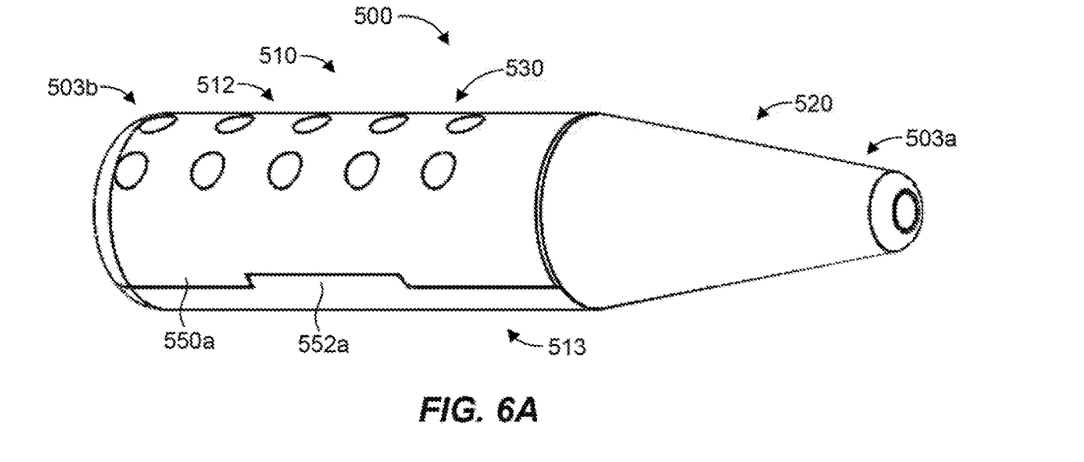
FIGS. 6A-6C illustrate aspects of a medical implant device in accordance with another example of the present disclosure.
Figure 6B:
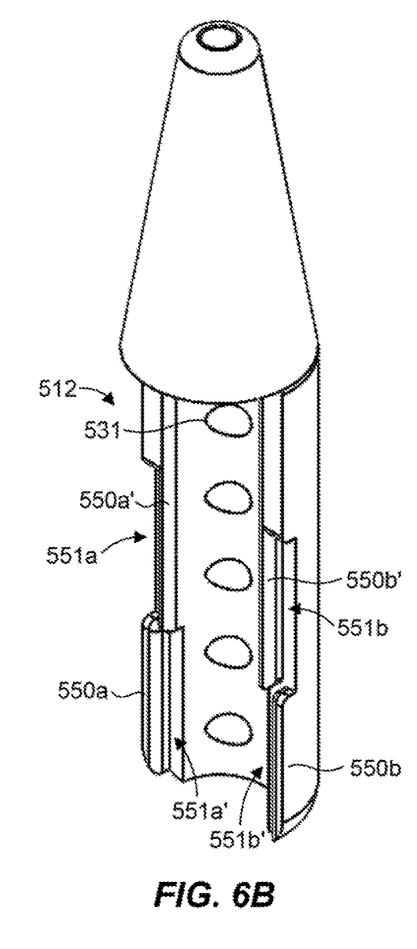
Figure 6C:
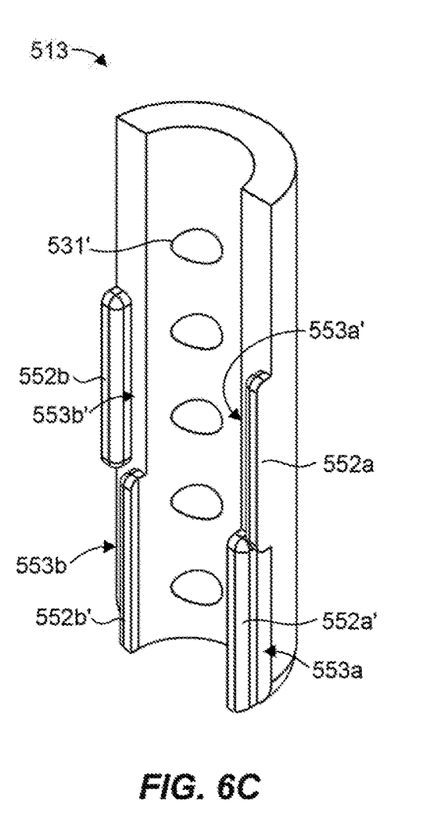

FIGS. 6A-6C illustrate aspects of a medical implant device or carrier 500 in accordance with another example of the present disclosure. In this case, the carrier 500 includes a payload receptacle 512 and a payload cover 513 with alignment features that are keyed along interfacing edges to facilitate proper alignment of the payload receptacle 512 and the payload cover 513 when coupled to one another. For example, the payload receptacle 512 can include one or more alignment tabs 550a, 550a', 550b, 550b' and/or one or more alignment recesses 551a, 551a', 551b, 551b'. The payload cover 513 can include one or more alignment tabs 552a, 552a', 552b, 552b' and/or one or more alignment recesses 553a, 553a', 553b, 553b' to mate with the alignment features of the payload receptacle 512. In one aspect, the alignment tabs can at least partially form or define the alignment recesses. On one lateral side of the carrier 500, the alignment tabs 550a, 550a' of the payload receptacle 512 can mate with the alignment recesses 553a, 553a', respectively, of the payload cover 513, and the alignment tabs 552a, 552a' of the payload cover 513 can mate with the alignment recesses 551a, 551a', respectively, of the payload receptacle 512. On another (e.g., opposite) lateral side of the carrier 500, the alignment tabs 550b, 550b' of the payload receptacle 512 can mate with the alignment recesses 553b, 553b', respectively, of the payload cover 513, and the alignment tabs 552b, 552b' of the payload cover 513 can mate with the alignment recesses 551b, 551b', respectively, of the payload receptacle 512.

In addition, a payload coupling interface 530 can be configured to couple an implant to the carrier 500 as well as secure the payload receptacle 512 and the payload cover 513 to one another. For example, the payload receptacle 512 and the payload cover 513 can each include one or more securing holes (indicated generally at 531, 531', respectively), which can facilitate securing an implant to the carrier 500 (e.g., to a main body portion 510) and coupling the payload receptacle 512 and the payload cover 513 to one another, such as with a suture. In other words, the same suture looped through securing holes in the payload receptacle 512 and the payload cover 513 can serve the dual purposes of securing an implant to the carrier 500 and securing the payload receptacle 512 and the payload cover 513 to one another. Thus, cutting such a suture can facilitate separating the payload receptacle 512 and the payload cover 513 from one another as well as release an implant from the carrier 500.

Figure 7A:
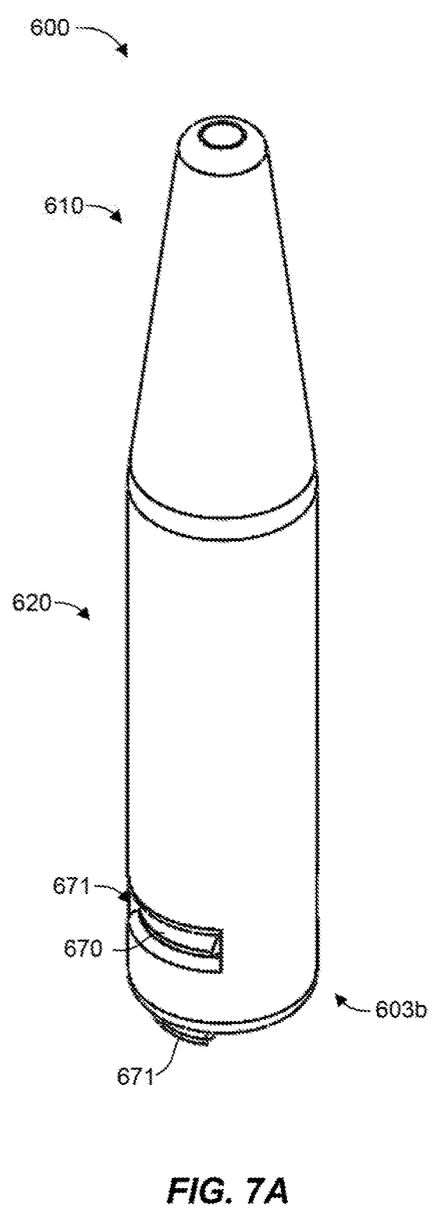
FIGS. 7A and 7B illustrate aspects of a medical implant device in accordance with another example of the present disclosure.
Figure 7B:
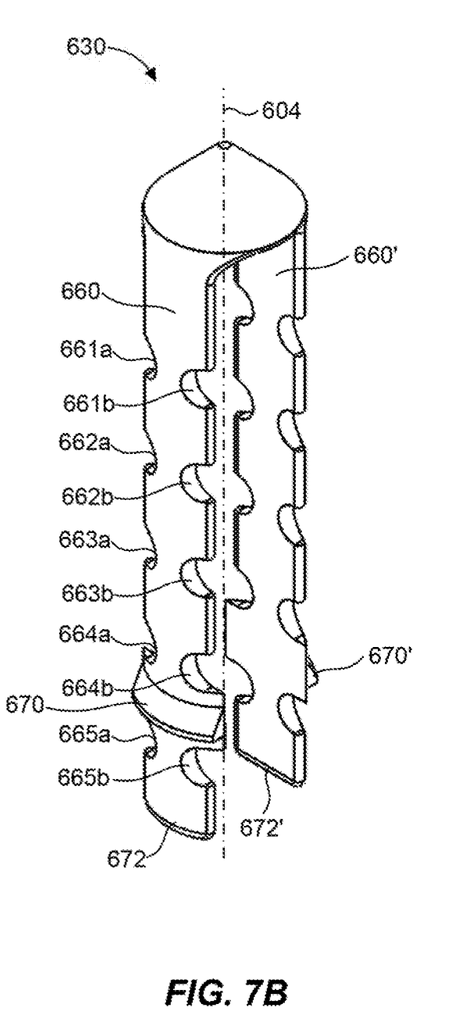

FIGS. 7A and 7B illustrate aspects of a medical implant device or carrier 600 in accordance with another example of the present disclosure. The carrier 600 is similar in many respects to carriers described above. For example, the carrier 600 can include a main body portion 610 and a tapered nose portion 620. The carrier 600 can also include a payload opening (obscured from view) that is exposed at a back end 603b of the carrier 600. The carrier 600 can further include a payload coupling interface 630 configured to couple an implant (not shown) to the carrier 600.

In this case, the payload coupling interface 630 can comprise an insert (FIG. 7B) configured to fit within the payload opening. The insert can be configured to be inserted into the payload opening via the back end 603b of the carrier 600. The insert can have one or more securing openings (e.g., a notch, a hole, etc.) to facilitate securing the implant to the insert, such as by tying with thread, (e.g., a surgical suture). In some embodiments, the insert can include securing portions 660, 660' that are parallel and spaced from one another to receive an implant between the securing portions 660, 660'. At least one of the securing portions 660, 660' can include a securing opening. For example, the securing portion 660 can include securing openings 661a-b, 662a-b, 663a-b, 664a-b, 665a-b. Primary reference will be made to the securing portion 660. The securing portion 660' can be similarly or differently configured (e.g., with a different securing opening configuration or no securing openings).

In some embodiments, securing openings can be configured as a pair of securing openings, with each of the securing openings in the pair located at the same longitudinal position of the insert. For example, the securing openings 661a-b can be arranged in a pair, the securing openings 662a-b can be arranged in a pair, the securing openings 633a-b can be arranged in a pair, the securing openings 664a-b can be arranged in a pair, and the securing openings 665a-b can be arranged in a pair. Each pair of securing openings 661a-b, 662a-b, 663a-b, 664a-b, 665a-b can be located at a different longitudinal position of the insert along a longitudinal axis 604 of the insert. This can provide multiple securing location options for securing an implant, and optionally a wire, to the insert and therefore to the carrier 600. In one aspect, at least one pair of securing openings of the securing portion 660 can be located at the same longitudinal position of the insert as at least one pair of securing openings of the securing portion 660'. Sutures can tie or otherwise couple an implant to one or both of the securing portions 660, 660' using any of the securing openings, such as securing openings 661a-b, 662a-b, 663a-b, 664a-b, 665a-b. The securing openings can prevent an implant from sliding relative to the insert.

The insert can hold an implant and can be coupleable to the main body portion 610 to couple the implant to the carrier 600. For example, the insert can include one or more detents 671, 671' and the carrier 600 can include one or more detent openings 670 to engage and interface with the detents to secure the insert to the main body portion 610, which can "snap" into the detent openings. The securing portions 660, 660' can each include an end 672, 672' that is configured to protrude from the main body portion 610 at the back end 603b of the carrier 600. These ends can be compressed, pinched, or squeezed together (e.g., by using a surgical tool, such as towel clamps) to release the detents from the detent openings. Alternatively, the detents 671, 671', which may be exposed through the detent openings, can be contacted directly and compressed inward to facilitate their release from the detent openings.

Although implants such as the USEA and Utah electrode array (UEA) are particularly exemplified, other fragile implants can also be used with the carriers described herein. Non-limiting examples of fragile implants can include UEA, USEA, Michigan arrays, LIFE, TIME, FINE, cuff, and spiral cuff electrodes. Fragile electrodes used in cardiovascular implants can also benefit from this device, as well as fragile electrodes implanted into muscle to record or stimulate their activity.

Figure 8:
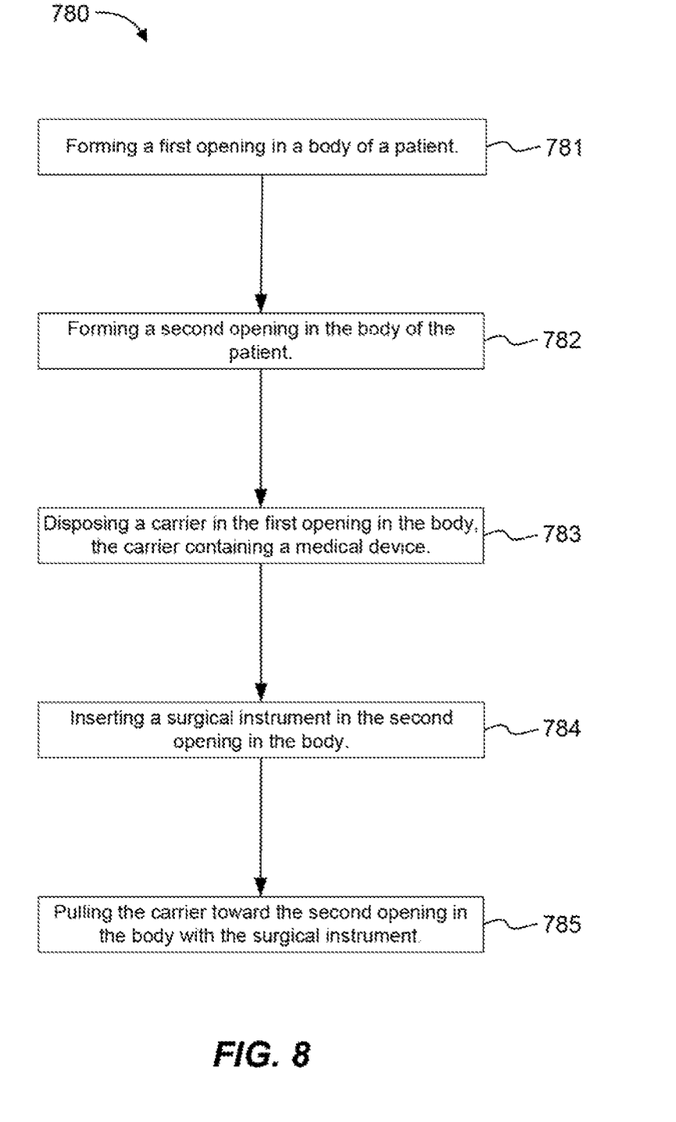
FIG. 8 is a flowchart of a method for implanting a medical device in accordance with an example of the present disclosure.
Figure 9:
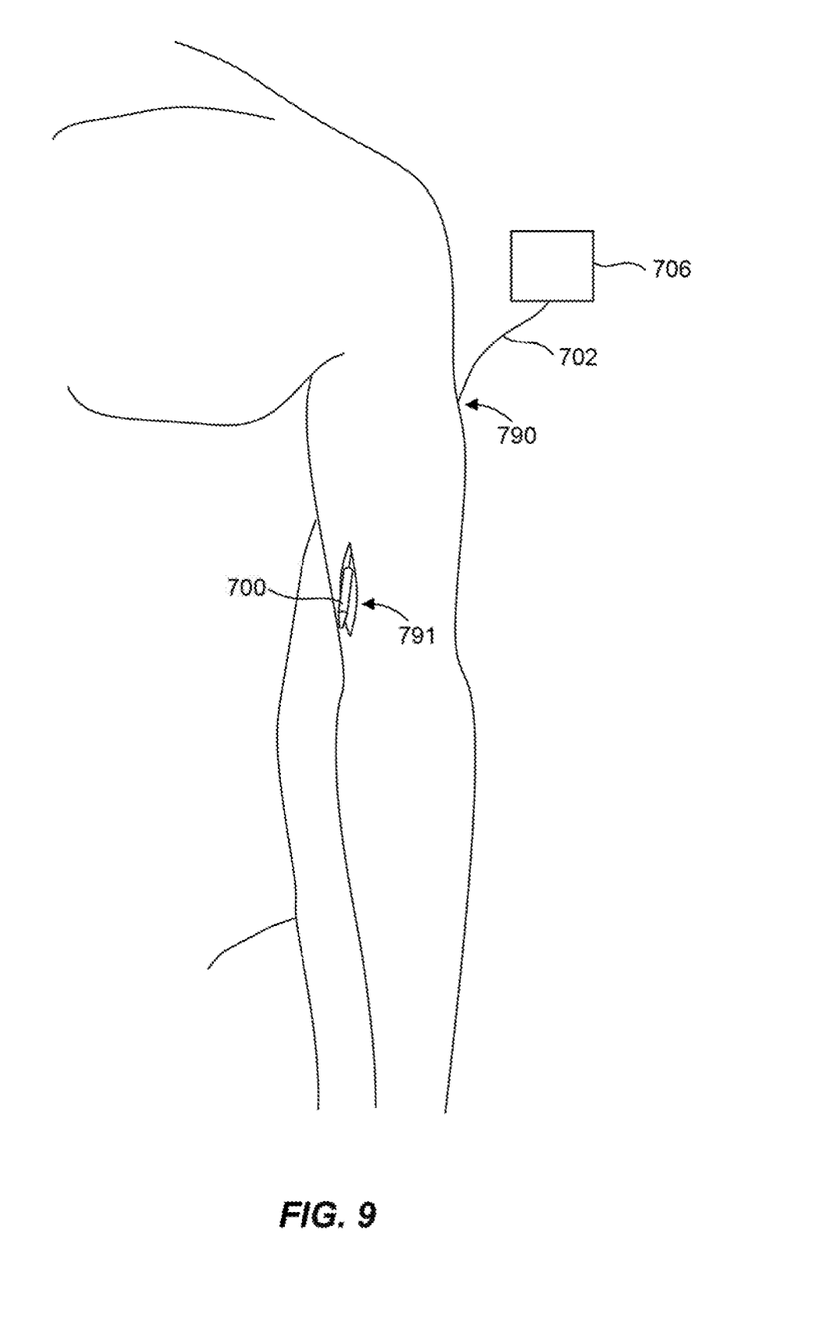
FIG. 9 illustrates a carrier at an implant location of a patient in accordance with an example of the present disclosure.

FIG. 8 illustrates a flowchart of a method 780 for implanting a medical device in accordance with an example of the present disclosure. The method can comprise forming a first opening in a body of a patient, shown at block 781. The location of the first opening may be selected as a desirable location for a wire extending from the medical device to exit the body. An example of a location of a first opening in a body of a patient is illustrated in FIG. 9 at 790. In this case, the location of the first opening is at an upper back or outside region of the patient's upper arm by the triceps. The method can also comprise forming a second opening in the body of the patient, shown at block 782. The location of the second opening may be proximate a final position of an implant. An example of a location of a second opening in a body of a patient is illustrated in FIG. 9 at 791. In this case, the location of the second opening is proximate to a desirable nerve interface location, which is at an inner portion of the patient's upper arm proximate to the biceps. The method can further comprise disposing a medical implant device (e.g., a carrier) in the first opening in the body, the medical implant device containing a medical device (e.g., an implant), shown at block 783. The method can still further comprise inserting a surgical instrument in the second opening in the body, shown at block 784. Additionally, the method can comprise pulling the medical implant device toward the second opening in the body with the surgical instrument, shown at block 785. In some embodiments, a medical device can have a wire 702 extending from the medical implant device 700 through the first opening in the body to couple with a control box 706, as shown in FIG. 9. Thus, the wire 702 can be "routed" through the body from the first opening to an implant location proximate the second opening. The carrier can protect the implant, which is coupled to an end of the wire, as the implant and wire are pulled through body tissue between the first and second openings in the patient's body. Although an implant coupled to a wire for connection to a control box is shown and described herein, it should be recognized that the present technology (e.g., the medical implant device or carrier) can be utilized to protect and shield any suitable implant or other medical device (i.e., wired or wireless) while moving through body tissue. The medical implant device or carrier can also facilitate movement of the implant through body tissue, such as by pulling, as described herein.

In one aspect, the method can further comprise disposing the implant in a payload opening of the carrier, and coupling the implant to the carrier. In a specific aspect, coupling the implant to the carrier can comprise securing the implant to the carrier with a suture. In another aspect, the method can further comprise removing the implant from the carrier. In a specific aspect, removing the implant from the carrier can comprise cutting a suture securing the implant to the carrier. These aspects are discussed above with reference to various examples of the present technology.

In one aspect, the carrier can have a similar function to a surgical trocar. The carrier may be made of sterilizable and biocompatible materials. It can be roughly bullet-shaped and can be completely hollow with openings at both ends. The implant can be secured with respect to the carrier via a securing mechanism or payload coupling interface. In one embodiment, the payload coupling interface can include two rows of holes (vias) on one side of the carrier in the cylindrical portion of the bullet. An implant can go into the wider portion of the carrier and can be secured to the inside by sutures looped around the implant and the vias. At least two suture loops may be needed on two different pairs of vias to properly secure the implant within the carrier. A surgeon can grab the smaller opening at the narrow end of the carrier with hemostats and pull the carrier through tissue, thereby bringing the implant to the implant site while protecting the fragile device. Once properly located, the surgeon can cut the suture with a scalpel and pull the carrier away from the now unsecured implant. The implant may be left at the implant site with no additional hardware.

The carrier can be attached to the implant before sterilization, allowing one sterilization step for both the implant delivery vehicle and the implant itself. In the operating room, the surgeon does not need to handle a trocar and move the implant into place. The surgeon can simply pull on the carrier to get the implant to its desired location without the need for additional hardware. Trocars can have trouble getting around tight corners. The carrier allows for greater freedom of rotation compared to a typical trocar allowing for the implant to be delivered through tissue that a traditional trocar may not be able to bore through. Some implantable devices are simply too fragile to risk having them break while they travel through the tunnel created by the trocar. Because the carrier prevents relative motion between the fragile implant and any other hardware until the device is at the implant site, it is easier to maintain highly fragile devices with this carrier. Furthermore, this device can be used with a tradition trocar. The carrier can be used to eliminate the relative motion between the trocar and implant during delivery to the implant site. This device is also 3D printable (assuming the printer can print in biocompatible and sterilizable plastics, and that the resulting print can withstand the mechanical loads a surgeon and the human body would apply during use). This allows for rapid design changes to make the best carrier possible for implants of varying form factor in a short amount of time. For example, length and diameter of the carrier can be varied based on the size of a corresponding implant device.

The carrier can be used in situations where use of a traditional trocar is impractical due to the fragility of the implant. Such applications can include, but are certainly not limited to: peripheral nerve interface implantation, EMG electrode implantation, Tendon transfer procedures, pacemaker electrode implants, and the like. Other procedures can also benefit from this technology. For example, orthopedic surgeons may use this device and delivery method if it benefits a procedure they regularly perform. It can also be used in parts of the body where a straight tunnel cannot be made with a trocar. This is especially prevalent where implants must be moved through tissue that is part of a large joint such as the elbow, knee, or hip.

The carrier can be useful when a device travels through tissue unexposed by the surgeon. If a very long trocar is needed, the tissue tunneling length limitation in length is defined by the longest available hemostats. However, use of the carrier in conjunction with a trocar can eliminate this issue, which may be useful for very fragile implants that travel a long distance through tissue. A significant amount of time is frequently used to properly secure the implants within the carrier. However, this can be done before the implant procedure and does not waste the surgeon's time. For the illustrated example, the carrier does not slide well going backwards, so once the carrier is positioned near the implant site, the carrier should not be dragged back out through the tissue. Alternatively, the carrier can be formed with a tapered trailing edge to allow backward movement through tissue. This can be accomplished as long as the opening is sufficient to accommodate the implant device. Alternatively, the carrier can be formed as a clamshell which is tapered at both ends and allows for simple insertion and removal of the implant from the carrier.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A medical implant device, comprising:
    a hollow main body portion having an internal cavity configured to house a payload and a payload opening configured to receive the payload into the internal cavity, wherein the main body portion is operable to shield and protect the payload within the main body portion as the main body portion and the payload travel through body tissue;
    a tapered nose portion at a front end of the medical implant device extending from the main body portion and configured to penetrate the body tissue as the main body portion and the payload travel through the body tissue;
    a payload coupling interface configured to couple the payload within the internal cavity to the main body portion; and
    an interface feature including one or more of:
        a) a manipulation interface at the front end of the medical implant device to facilitate grasping the medical implant device with a surgical instrument and pulling the medical implant device through the body tissue;
        b) wherein the payload coupling interface comprises a plurality of securing holes in the main body portion to facilitate securing the payload to the main body portion with a suture, wherein the plurality of securing holes comprises a pair of securing holes located at a same longitudinal position of the main body portion;
        c) wherein the payload coupling interface comprises an insert configured to fit within the payload opening, the insert having a securing opening to facilitate securing the payload to the insert with a suture; and
        d) wherein the main body portion comprises a payload receptacle and a payload cover that at least partially define the payload opening, the payload cover being movable relative to the payload receptacle to facilitate disposing the payload in the payload opening.

2. The medical implant device of claim 1, wherein the main body portion and the tapered nose portion are integrally formed with one another in a monolithic structure.

3. The medical implant device of claim 1, wherein the payload opening is exposed at a back end of the medical implant device opposite the front end.

4. The medical implant device of claim 1, wherein the manipulation interface is present and comprises an outer surface of the tapered nose portion and an inner surface of the tapered nose portion, the inner surface being defined at least partially by a front opening in the tapered nose portion exposed at the front end of the medical implant device.

5. The medical implant device of claim 4, wherein the outer and inner surfaces of the tapered nose portion are oriented at an angle relative to one another from about 10 degrees to about −10 degrees.

6. The medical implant device of claim 1, wherein the manipulation interface is present and comprises a tab extending from the front end of the tapered nose portion.

7. The medical implant device of claim 1, wherein the tapered nose portion comprises a conical shaped outer surface.

8. The medical implant device of claim 1, wherein the plurality of securing holes is present and comprises a plurality of pairs of securing holes, each pair of securing holes located at a different longitudinal position of the main body portion, and wherein the plurality of pairs of securing holes are located on a same side of the main body portion.

9. The medical implant device of claim 1, wherein the payload opening is exposed at a back end of the medical implant device, and the insert is configured to be inserted into the payload opening via the back end of the medical implant device.

10. The medical implant device of claim 1, wherein the insert comprises first and second securing portions parallel and spaced from one another to receive the payload therebetween, at least one of the securing portions including the securing opening, wherein the securing opening comprises a plurality of securing openings including a pair of securing openings located at a same longitudinal position of the insert.

11. The medical implant device of claim 10, wherein the plurality of securing openings comprises a first plurality of pairs of securing openings in the first securing portion and a second plurality of pairs of securing openings in the second securing portion, each pair of securing openings of the first plurality of pairs being located at a different longitudinal position of the insert, and each pair of securing openings of the second plurality of pairs being located at a different longitudinal position of the insert.

12. The medical implant device of claim 1, wherein the securing opening comprises a notch.

13. The medical implant device of claim 1, wherein the insert is coupleable to the main body portion via a detent.

14. The medical implant device of claim 1, wherein the payload receptacle and the payload cover comprise longitudinally oriented openings configured to be aligned with one another, and wherein a removable coupling member is configured to be disposed in the longitudinally oriented openings to secure the payload cover and the payload receptacle to one another.

15. The medical implant device of claim 1, wherein the payload receptacle and the payload cover are removably coupleable with one another.

16. The medical implant device of claim 15, wherein the payload receptacle and the payload cover comprise first longitudinally oriented openings configured to be aligned with one another, and second longitudinally oriented openings configured to be aligned with one another, the first and second longitudinally oriented openings being located on opposite lateral sides of the medical implant device, and wherein a first removable coupling member is configured to be disposed in the first longitudinally oriented openings and a second removable coupling member is configured to be disposed in the second longitudinally oriented openings to removably couple the payload receptacle and the payload cover to one another.

17. The medical implant device of claim 15, wherein the payload cover comprises at least one of an alignment tab and an alignment recess, and the payload receptacle comprises the other of the at least one of the alignment tab and the alignment recess to facilitate proper alignment of the payload cover and the payload receptacle when coupled to one another.

18. The medical implant device of claim 1, wherein the payload coupling interface comprises a protrusion extending from at least one of the payload receptacle and the payload cover that defines the payload opening toward a back end of the medical implant device such that movement of the payload toward the back end of the medical implant device is prevented.

19. The medical implant device of claim 18, wherein the protrusion is configured to accommodate a wire from the payload extending out a back end of the medical implant device.

20. The medical implant device of claim 1, wherein the interface feature includes only (a) of (a) through (d).

21. The medical implant device of claim 1, wherein the interface feature includes only (b) of (a) through (d).

22. The medical implant device of claim 1, wherein the interface feature includes only (c) of (a) through (d).

23. The medical implant device of claim 1, wherein the interface feature includes only (d) of (a) through (d).

24. A method for implanting a medical device, comprising:
forming a first opening in a body of a patient;
forming a second opening in the body of the patient;
disposing the medical implant device of claim 1 in the first opening in the body, the medical implant device, wherein the payload is the medical device;
inserting a surgical instrument in the second opening in the body; and
pulling the medical implant device toward the second opening in the body with the surgical instrument.

25. The method of claim 24, wherein the medical device comprises a wire extending from the medical implant device through the first opening in the body and the method further comprises:
disposing the medical device in a payload opening of the medical implant device; and
coupling the medical device to the medical implant device.

26. The method of claim 25, wherein coupling the medical device to the medical implant device comprises securing the medical device to the medical implant device with a suture.

27. The method of claim 24, further comprising removing the medical device from the medical implant device.

* * * * *